United States Patent [19]

Harnden et al.

[11] Patent Number: 5,108,994
[45] Date of Patent: * Apr. 28, 1992

[54] ANTIVIRAL PURINE DERIVATIVES

[75] Inventors: Michael R. Harnden; Leslie J. A. Jennings, both of Epsom, England

[73] Assignee: Beecham Group p.l.c., Brentford, England

[*] Notice: The portion of the term of this patent subsequent to Oct. 8, 2008 has been disclaimed.

[21] Appl. No.: 528,575

[22] Filed: May 23, 1990

Related U.S. Application Data

[63] Continuation-in-part of Ser. No. 387,068, Jul. 28, 1989, Pat. No. 5,055,458, and a continuation-in-part of Ser. No. 276,868, Nov. 28, 1988, abandoned.

[30] Foreign Application Priority Data

May 25, 1989 [GB] United Kingdom ................ 8912043

[51] Int. Cl.$^5$ .................. A61K 31/675; C07D 9/6561
[52] U.S. Cl. ..................... 514/81; 544/243; 544/244; 556/405; 558/189
[58] Field of Search ................. 544/243, 244; 514/81, 514/86

[56] References Cited

U.S. PATENT DOCUMENTS

| | | | |
|---|---|---|---|
| 4,360,522 | 11/1982 | Schaeffer | 544/244 X |
| 4,755,516 | 7/1988 | Tolman et al. | 514/262 |
| 4,806,642 | 2/1989 | Sircar et al. | 544/244 |
| 4,808,716 | 2/1989 | Holy et al. | 544/244 |
| 4,910,307 | 3/1990 | Wyatt | 544/276 |
| 4,965,270 | 10/1990 | Harnden et al. | 514/262 |
| 5,055,458 | 10/1991 | Bailey et al. | 514/81 |

FOREIGN PATENT DOCUMENTS

| | | | |
|---|---|---|---|
| 0294069 | 12/1988 | European Pat. Off. | 544/277 |
| 0298601 | 1/1989 | European Pat. Off. | 544/277 |
| 0313289 | 4/1989 | European Pat. Off. | 544/277 |
| 0319228 | 6/1989 | European Pat. Off. | 544/244 |
| 0353955 | 2/1990 | European Pat. Off. | 544/244 |

OTHER PUBLICATIONS

Prisbe et al., J. Med. Chem., vol. 29 (5), pp. 671-675 (May/1986).
Duke et al., Antiviral Research, vol. 6, pp. 299-308 (1986).
Striecher et al., Chemica Scripta, vol. 26, pp. 179-183 (1986).

Primary Examiner—Diana G. Rivers
Attorney, Agent, or Firm—Hopgood, Calimafde, Kalil, Blaustein & Judlowe

[57] ABSTRACT

Compounds of formula (I), and pharmaceutically acceptable salts thereof:

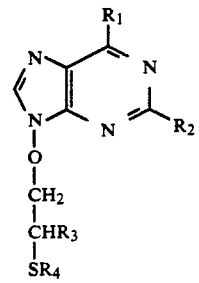

wherein
$R_1$ is hydroxy or amino;
$R_2$ is hydrogen or amino;
$R_3$ is hydrogen, hydroxymethyl or acyloxymethyl;
$R_4$ is a group of formula:

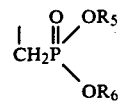

wherein
$R_5$ and $R_6$ are independently selected from hydrogen, $C_{1-6}$ alkyl and optionally substituted phenyl; or
$R_3$ and $R_4$ together are:

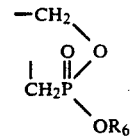

wherein
$R_6$ is as defined above;
having antiviral activity, processes for their preparation and their pharmaceutical use.

8 Claims, No Drawings

ANTIVIRAL PURINE DERIVATIVES

This application is a continuation-in-part of application Ser. No. 276,868, filed Nov. 28, 1988, now abandoned, and of application Ser. No. 387,068, filed Jul. 28, 1989, the disclosures of which are incorporated herein by reference.

The present invention relates to compounds having antiviral activity, to processes for their preparation and to their use as pharmaceuticals.

EP-A-242482 (Beecham Group p.l.c.) describes a group of guanine derivatives having a 9-hydroxyalkoxy substituent, and possessing antiviral activity.

A novel, structurally distinct class of compounds has now been discovered, these compounds also having antiviral activity.

Accordingly, the present invention provides a compound of formula (I), or a pharmaceutically acceptable salt thereof:

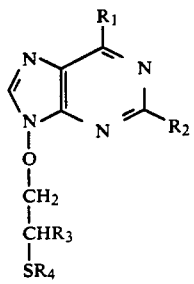

wherein
$R_1$ is hydroxy or amino;
$R_2$ is hydrogen or amino;
$R_3$ is hydrogen, hydroxymethyl or acyloxymethyl;
$R_4$ is a group of formula:

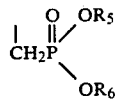

wherein
$R_5$ and $R_6$ are independently selected from hydrogen, $C_{1-6}$ alkyl and optionally substituted phenyl; or $R_3$ and $R_4$ together are:

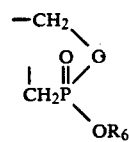

wherein
$R_6$ is as defined above.

When $R_1$ is hydroxy and $R_2$ is amino, the compound of formula (I) is a guanine derivative;

When $R_1$ is amino and $R_2$ is hydrogen, the compound of formula (I) is an adenine derivative;

When $R_1$ is hydroxy and $R_2$ is hydrogen, the compound of formula (I) is a hypoxanthine derivative; and When $R_1$ and $R_2$ are both amino groups, the compound of formula (I) is a 2,6-diaminopurine derivative.

Often, the compound of formula (I) is a guanine or adenine derivative.

Suitable examples of the acyl group in $R_3$ when acyloxymethyl, include carboxylic acyl, such as $C_{1-7}$ alkanoyl and benzoyl optionally substituted in the phenyl ring as defined below for $R_5/R_6$. Preferred acyl groups include acetyl, propionyl, butyryl, heptanoyl and hexanoyl.

Suitable examples of $R_5$ and $R_6$ include hydrogen, methyl, ethyl, n- and iso-propyl, n-, sec-, iso- and tert-butyl, and phenyl optionally substituted by one, two or three groups or atoms selected from halogen, such as fluoro, chloro, bromo, and $C_{1-4}$ alkyl or $C_{1-4}$ alkoxy wherein the alkyl moiety is selected from those listed for $R_5/R_6$ above.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

As the compound of formula (I) contains a phosphonate group, suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine.

It will be appreciated that some of the compounds of formula (I), especially those wherein $R_3$ is other than hydrogen, have an asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

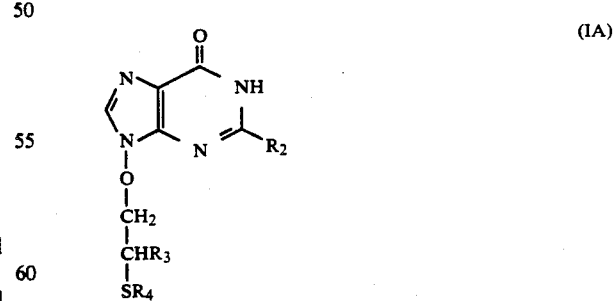

The invention also provides a process for the preparation of a compound of formula (I), or a pharmaceutically acceptable salt thereof, which process comprises either (i) imidazole ring closure of a compound of formula (II):

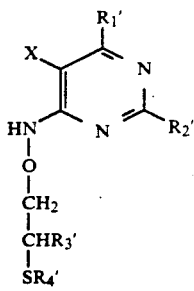

wherein X is a group capable of cyclising to form an imidazole ring, such as amino or an amino derivative, for example, formylamino; or (ii) pyrimidine ring closure of a compound of formula (III)

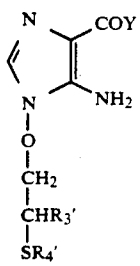

wherein Y is amino or $C_{1-6}$ alkoxy, with a condensing agent capable of cyclising to form a pyrimidine ring having a 2-$R_2$ substituent, to give a compound of formula (I) wherein $R_1$ is hydroxy and $R_2$ is amino; or (iii) condensing a compound of formula (IV):

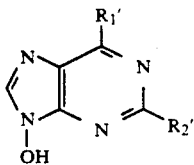

with a side chain intermediate of formula (V):

$$QCH_2CHR_3'SR_4' \quad (V)$$

wherein Q is a leaving group; and wherein, in formulae (II) to (V), $R_1'$, $R_2'$, $R_3'$ andl $R_4$ 'are $R_1$, $R_2$, $R_3$ and $R_4$ respectively, or groups or atoms convertible thereto; and thereafter, when desired or necessary, converting $R_1'$, $R_2'$, $R_3'$ and/or $R_4'$, when other than $R_1$, $R_2$, $R_3$ and/or $R_4$ to $R_1$, $R_2$, $R_3$ and/or $R_4$ respectively, and/or converting $R_1'$, $R_2'$, $R_3'$ amd/or $R_4'$ when $R_1$, $R_2$, $R_3$ and/or $R_4$, to other $R_1$, $R_2$, $R_3$ and/or $R_4$.

Process (i) may be carried out, preferably when X is formylamino, using a cyclisation condensing agent, such as diethoxymethyl acetate or triethyl orthoformate, or by fusion.

Process (ii) is preferably carried out in accordance with the methods described in EP-A-242482, the subject matter of which is incorporated herein by reference.

Process (iii) may be carried out with suitable values for Q including halo, such as chloro, bromo and iodo, preferably iodo; or other groups readily displaceable by nucleophiles, such as mesyloxy or tosyloxy. The reaction preferably takes place in an inert solvent, such as dimethylformamide in the presence of a base, such as potassium carbonate, at 0°–50° C., preferably ambient temperature. Alternatively, Q may be OH, in which case the reaction takes place in the presence of a dehydrating catalyst, such as diethyl azodicarboxylate in the presence of triphenylphosphine.

Examples of conversions of variable groups are as follows:

$R_1'$-$R_1$ (a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Ozanski Can. J. Chem, 59, 2601 (1981).

(b) An $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°–150° C., preferably around 100° C.

(c) An $R_1'$ chloro group may be converted to $R_1$ is amino by treatment with ammonia in a lower alkanol, such as ethanol or methanol in an autoclave at 100° C. for a period of about 7 hours, or alternatively, by treatment with sodium azide in dimethylformamide (forming an $R_1$ is $N_3$ intermediate), followed by reduction with ammonium formate/palladium on charcoal, in methanol.

(d) An $R_1'$ alkoxy group, such as methoxy, may be converted to $R_1$ hydroxy by the methods of D. R. Haines, J. Med. Chem. 1987, 30, 943 and K. K. Ogilvie and H. R. Hanna, Can. J. Chem. 1984, 62, 2702.

(e) An $R_1'$ protected amino group, such as tritylamino, may be converted to amino, by treatment with aqueous acetic acid, preferably 80% acetic acid at elevated temperature, around 80° C. $R_1'$ may also be phthalimido, which may be converted to amino by treatment with methyl hydrazine or hydrazine in an inert solvent, such as dichloromethane, at ambient temperature.

$R_2'$-$R_2$ (a) $R_2'$ may be protected amino, such as formylamino, which may be converted to $R_2$ is amino by hydrolysis; or $R_2'$ may be di-t-butyloxycarbonylamino.

$R_3'$-$R_3$ (a) Hydroxy or hydroxymethyl may be converted to acyloxy or acyloxymethyl respectively by conventional acylation procedures.

(b) Protected hydroxy or protected hydroxymethyl may be converted to hydroxy or hydroxymethyl by conventional deprotection methods.

Suitable examples of protecting groups and their removal, are as described in EP-A-242482. A particularly suitable protecting group is the acetyl group removable by hydrolysis.

$R_4'$-$R_4$

When $R_5$ and $R_6$ in $R_4$ are other than hydrogen, they may be converted to $R_5$ and $R_6$ are hydrogen, using a deesterifying reagent, such as trimethylsilyl bromide in an aprotic solvent such as dichloromethane or dimethylformamide at ambient temperature, as described by C. E. McKenna et. al. J.C.S. Chem. Comm., 1979, 739.

Selective conversion of one of $R_5$ and $R_6$ to hydrogen, may be achieved by treatment with hydroxide ion, as described by Rabinowitz JACS 1960, 82. 4564.

Cyclic phosphonates wherein $R_3$ and $R_4$ are joined together as defined, may be prepared from the corresponding compound of formula (I) wherein $R_5$ or $R_6$ is hydrogen and $R_3$ is hydroxy, by reaction with N,N-dicyclohexyl-4-morpholinocarboxamidine and a dehydrating reagent, such as dicyclohexylcarbodiimide.

It will be appreciated that the above conversions may take place in any desired or necesssary order, having regard to the final desired compound of formula (I).

Intermediates of formula (II) may be prepared from a corresponding compound of formula (VI):

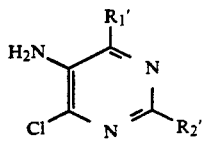
(VI)

and via intermediates of formula (V) wherein Q is OH, as hereinbefore defined, according to the methods described in EP-A-242482 i.e. by converting the compound of formula (V) wherein Q is OH to the phthalimidooxy derivative followed by reaction with methylhydrazine.

The compound of formula (VI) wherein $R_1'$ is cloro and $R_2'$ is amino, is a known compound as described by Temple et. al. J. Org. Chem., 40 (21), 3141, 1975.

The compound of formula (VI) wherein $R_1'$ is chloro and $R_2'$ is hydrogen is a commercially available compound.

Intermediates of formula (III) may be prepared according to the methods generally described in EP-A-242482.

Compounds of the formula (IV) are prepared as described in EP-A-313289 and EP-A-319228, from compounds of formula (VI) wherein the 5-amino group is formylated, by reaction with $R_7ONH_2$ wherein $R_7$ is a protecting group, to give a compound of formula (VII):

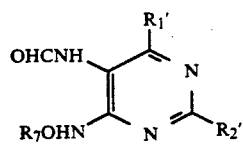
(VII)

which may be cyclised with diethoxymethyl acetate, to give a compound of formula (IV) wherein the OH group is protected. Suitable values for $R_7$ include benzyl, removable by hydrogenation, and the tetrahydropyran-2-yl group removable by treatment with 80% acetic acid, at ambient temperature.

Intermediates of the formula (V) wherein Q is hydroxy are known compounds or are prepared by analogous methods to those used for structurally similar known compounds.

When $R_3$ is hydrogen, they may be prepared by reacting the appropriate $R_4'Cl$ with thioethanol in the presence of a base such as sodium hydride/potassium iodide, in an inert solvent such as tetrahydrofuran, as in Description 1 hereinafter.

The compound of formula (V) wherein $R_3'$ is hydroxymethyl may then be prepared as follows:

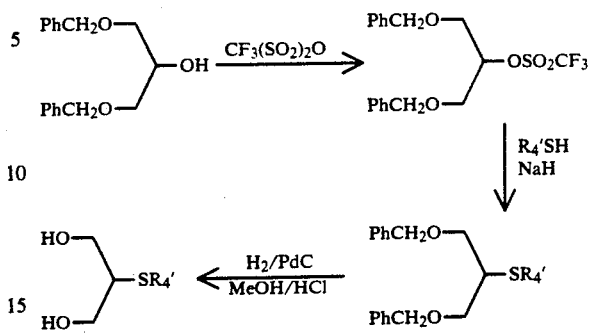

When $R_3$ is hydroxymethyl, selective protection on one of the hydroxy groups in the side chain intermediate of formula (V) is required. This is achieved by reacting with trimethylorthoformate in the presence of an acid catalyst, such as p-toluenesulphonic acid.

Pharmaceutically acceptable salts may be prepared in conventional manner, for example, in the case of acid addition salts, by reaction with the appropriate organic or inorganic acid.

It will be appreciated that the invention provides a process for the preparation of a compound of formula (I) wherein $R_3$ is hydroxymethyl which process comprises the deprotection of a corresponding compound of formula (I) wherein $R_3$ is protected hydroxymethyl. Preferred methods for deprotection, as hereinbefore described, include removal of the acetyl group.

The invention also provides a process for the preparation of a compound of formula (I) wherein $R_5$ and $R_6$ are both hydrogen, which process comprises the deesterification of a corresponding compound of formula (I) wherein $R_5$ and $R_6$ are the same alkyl or optionally substituted phenyl group.

The compounds of the invention are of potential use in the treatment of infections caused by viruses, in particular DNA viruses and retroviruses. Examples of DNA viruses include herpesviruses such as herpes simplex types 1 and 2, varicella-zoster virus, Epstein-Barr virus and cytomegalovirus. Examples of retroviruses include lentiviruses such as visna virus and human immunodeficiency virus (strains 1 and 2).

The compounds may also be inhibitors of tumorogenic viruses and/or of potential use in the treatment of neoplastic diseases, i.e. cancer.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, nontoxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention are also believed to exhibit a synergistic antiviral effect in conjunction with interferons; and combination products comprising these two components for sequential or concomitant administration, by the same or different routes, are therefore within the ambit of the present invention.

The following examples illustrate the invention; the following descriptions illustrate the preparation of intermediates.

DESCRIPTION 1

(Intermediate (V) for Examples 1–4)

Diethyl 2-hydroxyethylthiomethylphosphonate

Sodium hydride (1.5g, 80%, 50 mmol) was added in portions to a stirred solution of thioethanol (3.9 g, 50 mmol) in dry tetrahydrofuran (50 ml) at room temperature. The mixture was stirred for 0.5 hours then freshly ground and dried potassium iodide (0.5 g, 3.0 mmol) was added, followed by diethylchloromethylphosphonate (9.3 g, 50 mmol) in dry tetrahydrofuran (25 ml) over 5 minutes (exothermic reaction, temperature rose to 50° C.). The reaction mixture was then stirred and heated at 80° C. for 18 hours. The cooled reaction was evaporated to dryness in vacuo, and the residue was purified by column chromatography on silica gel eluting with chloroform, to give the title compound as an oil (8.0 g, 79%); $\upsilon_{max}$ (Film) 3380, 2980, 2900, 2860, 1475 and 1440 cm$^{-1}$; $\delta_H$(CDCl$_3$) 1.35 (6H, t, J 7Hz, 2 × CH$_3$), 2.80 (2H, d, J 13Hz, PCH$_2$S), 2.87 (2H, t, J 5Hz, SCH$_2$CH$_2$), 3.8 (2H, br s, CH$_2$OH), 3.92 (1H, br s, D$_2$O exchangeable, OH), 4.2 (4H, m, 2 × CH$_2$OP), (Found: C, 35.43; H, 7.64%, MH$^+$ NH$_3$ CI 229. C$_7$H$_{17}$O$_4$PS.0.5H$_2$O requires C, 35.46; H, 7.64%, M$^+$ 228).

DESCRIPTION 2 (Intermediate (II) for Examples 1 and 2)

(a) N-(2-Diethoxyphosphorylmethylthio)ethoxyphthalimide

Diethylazodicarboxylate (3.8 g, 22 mmol) was added to a stirred solution of diethyl 2-hydroxyethylthiomethylphosphonate (4.5 g, 20 mmol), N-hydroxyphthalimide (3.26 g, 20 mmol) and triphenylphosphine (5.78 g, 22 mmol) in dry dimethylformamide (50 ml) at 0.5° C. The mixture was then stirred at room temperature for 18 hours. The solvent was removed in vacuo and the residue was dissolved in diethyl ether (75 ml) and cooled to 0°–5° C. for 5 hours. The solid was filtered off and the filtrate was evaporated to dryness in vacuo, the residue was purified by column chromatography on silica gel eluting with diethyl ether, to give the title compound (5.3 g, 71%) as a pale oil; $\upsilon_{max}$ (Film) 2970, 2920, 2900, 1730, 1460 and 1435 cm$^{-1}$; $\delta_H$(CDCl$_3$) 1.35 (6H, t, J 7Hz, 2 × CH$_3$), 2.85 (2H, d, J 13Hz, PCH$_2$S), 3.13 (2H, t, J 6.5Hz, CH$_2$S), 4.20 (4H, m, 2 x CH$_2$OP), 4.42 (2H, t, J 6.5Hz, CH$_2$ON), 7.80 (4H, m, Ar) (Found: M$^+$ 373.0751 C$_{15}$H$_{20}$NO$_6$SP requires M$^+$ 373.0749).

(b) Diethyl 2-aminooxyethylthiomethylphosphonate

Methyl hydrazine (0.56 g, 12 mmol) was added to a solution of N-(2-diethyloxyphosphorylmethylthio)ethoxy phthalimide (3.0 g, 8 mmol) in dry dichloromethane at 0°–5° C. The mixture was stirred for 2 hours, then filtered and the solvent was evaporated in vacuo. The residue was purified by chromatography on silica gel eluting with ethyl acetate: methanol (97:3) to give the title compound as an oil (1.6 g, 84%); $\upsilon_{max}$ (Film) 3460, 3300, 2980, 2890, 1590, 1470, 1440, 1385, and 1365 cm$^{-1}$; $\delta_H$ [CD$_3$)$_2$SO] 1.24 (6H, t, J6.5Hz, 2 × CH$_3$), 2.83 (2H, t, J 6.5Hz, CH$_2$S) 2.90 (2H, d, J 13Hz PCH$_2$S), 3.68 (2H, t, J 6.5Hz, CH$_2$ONH$_2$), 4.03 (4H, m 2 x CH$_2$OP), 6.0 (2H, br.s, D$_2$O exchangeable, NH$_2$). (Found: C, 34.95; H, 7.40; N, 5.63% C$_7$H$_{18}$NO$_4$PS requires C, 34.56; H, 7.45; N, 5.76%).

(c) 4-Chloro-6-[(2-diethoxyphosohorylmethylthio)ethoxy]amino-2,5-diformamidopyrimidine A solution of diethyl 2-aminooxyethylthiomethylphosphonate (1.6 g, 6.6 mmol), 4,6-dichloro-2,5-diformamidopyrimidine (1.54 g, 6.5 mmol) and diisopropylethylamine (1.7 g, 13 mmol) in dry diglyme (10 ml) was heated to 100° C. for 2.5 hours. The cooled reaction was then filtered and the solvent was evaporated in vacuo, the residue was purified by column chromatography on silica gel eluting with dichloromethane: methanol (97:3) to give the title compound as a yellow oil. (6.9 g, 30%) $\lambda_{max}$ (MeOH) 226 and 287mm ($\epsilon$ 9750 and 12656); $\upsilon_{max}$ (Film) 3200, 2970, 2920, 1700, 1690, 1585, 1475 and 1415 cm$^{-1}$; $\delta_H$[CD$_3$)$_2$SO] 1.23 (6H, t, J 6.5Hz, 2 × CH$_3$), 2.9 (4H, m, PCH$_2$S and CH$_2$S), 4.0 (6H, m 2 x CH$_2$OP and CH$_2$ON), 8.14 (1H, s, ONH), 9.26 (1H, br.s, CHO), 9.4 (1H, br.s, D$_2$O exchangeable NH), 10.8 (2H, m, D$_2$O exchangeable NH+CHO). (Found: M$^+$, 441.0633. C$_{13}$H$_{21}$N$_5$O$_4$SPCl requires M$^+$ 441.0639).

DESCRIPTION 3

(intermediate (V) for Examples 5–9)

(a)

1,3-Dibenzyloxypropan-2-oxy-trifluoromethanesulphonate

A solution of 1,3-dibenzyloxypropanol (5.4 g, 20 mmol) and 4-dimethylaminopyridine (3.0 g, 20 mmol) in dry dichloromethane (75 ml) was treated with trifluoromethansulphonic anhydride (6.7 g, 24 mmol) at 0°–5° C. The mixture was stirred for 1 hour and then washed with cold water, dried (MgSO$_4$), filtered and the solvent evaporated in vacuo. The residue was purified by column chromatography on silica gel, using ethyl acetate: hexane (50:50 as eluent, to give the title compound as a pale oil (6.6 g 82.5%); $\upsilon_{max}$ (Film), 3090, 3060, 3020, 2870, 1610, 1590, 1500, 1455, 1410 cm$^{-1}$; $\delta_H$ (CDCl$_3$) 3.65 (4H, d, J 7Hz, 2 × OCH$_2$) 4.5, (4H, s, PhCH$_2$), 5.1 (1H, quintet J 7Hz, CH); 7.3 (10H, m, ArH).

(b) Diethyl 1,3-dibenzyloxypropan-2-thiomethylphosphonate

A solution of diethylmethylphosphonate (1.1 g, 6 mmol) in dry tetrahydrofuran (20 ml) was treated with sodium hydride (0.15 g, 6.25 mmol) at 0°–5° C. stirred for 1 hour at room temperature. The solution was then cooled to 0°–5° C. and treated with a solution of 1,3-dibenzyloxypropan-2-oxy-trifluoromethanesulphonate (2.65 g, 6.5 mmol) in dry tetrahydrofuran (10 ml). The reaction mixture was then stirred at room temperature for 3 hours. The solvent was removed in vacuo and the residue was purified by column chromatography on silica, using ethyl acetate: hexane (60:40), to give the title compound as a colourless oil (1.9 g, 74%); $\upsilon_{max}$ (Film) 3060, 3015, 2980, 2905, 2860, 1960, 1875, 1810, 1605, 1590, 1495, 1475, 1450, 1390, and 1365 cm$^{-1}$; $\delta_H$ (CDCl$_3$) 1.3 (6H, t, J 7Hz, 2 x CH$_3$), 2.85 (2H, d J 13Hz, PCH$_2$S), 3.4 (1H, m, CH), 3.7 (4H, d J 7Hz, 2 × CH$_2$O), 4.15 (4H, m, 2 × CH$_2$), 4.5 (4H, s, CH$_2$Ph), and 7.3 (10H, m, Ar H) (Found: C, 60.41; H, 7.33%. C$_{22}$H$_{31}$O$_5$PS requires C, 60.25; H, 7.12%).

(c) Diethyl 1,3-dihydroxypropan-2-thiomethylphosphonate

A solution of diethyl 1,3-dibenzyloxypropan-2-thiomethylphosphonate (1.5 g, 3.4 mmol) in methanol (20 ml) was treated with methanolic hydrogen chloride (0.5 ml) and hydrogenated at S.T.P over 10% palladium on charcoal (1.7 g) until hydrogen uptake ceased (122 ml H$_2$ 36 ml catalyst uptake). The reaction mixture was filtered and the solvent evaporated in vacuo. The residue was purified by column chromatography on silica using dichloromethane: methanol (95:5) as eluent to give the title compound as a colourless oil (0.7 g, 80%); $\upsilon_{max}$. (Film) 3400, 2990, 2940, 2920, 2880, 1650, 1472, 1445, 1320 and 1390 cm$^{-1}$; $\delta$H [(CD)$_3$SO] 1.24 (6H, t, J 7Hz 2 × CH$_3$), 2.9 (2H, d, J 13Hz PCH$_2$S), 2.91 (1H, m, CH), 3.6 (4H, m, 2 × CH$_2$OH), 4.0 (4H, m, 2 × CH$_2$), 4.7 (2H, t J 5.5Hz D$_2$O exchangeable 2 × OH) (Found: C, 36.39; H, 7.65%; MH+, 259.0766. C$_8$H$_9$O$_5$PS requires C, 37.20; H, 7.41%; MH+, 259.0769).

(d) Diethyl 1-acetoxy-3-hydroxypropan-2-thiomethylphosphonate

A solution of diethyl 1,3-dihydroxypropan-2-thiomethylphosphonate (2.1 g, 8.1mmol) in dry tetrahydrofuran (30 ml) was treated with trimethylorthoformate (3.7 g 30 mmol) and p-toluenesulphonic acid (0.2 g, 1mmol) and stirred at room temperature for 18 hours. 5M hydrochloric acid (5 drops) was added and stirring continued for a further 20 minutes. The solvent was evaporated in vacuo and the residue purified by column chromatography on silica, using chloroform as eluent, to give the title compound as a colourless oil (1.8 g, 75%); $\upsilon_{max}$ (Film) 3400, 2980, 2930, 1740, 1440, 1380 and 1240 cm$^{-1}$; $\delta$H [(CD$_3$)$_2$SO] 1.24 (6H, t, J 7Hz, 2 × CH$_3$), 2.0 (3H, s, CH$_3$), 2.95 (2H, d, J 13, PCH$_2$S), 3.2 (1H, m, CH), 3.6 (2H, m, CH$_2$OH), 4.1 (4H, m, 2 × CH$_2$), 4.2 (2H, m, CH$_2$OAc) 4.9 (1H, t J 5.5Hz exchangeable with D$_2$O, OH), Found: C, 39.39; H, 7.23%. C$_{10}$H$_{21}$O$_6$PS requires C, 40.00; H, 7.05%).

DESCRIPTION 4

(Intermediate (V) for Examples 12 and 13)

(a) (R)-1-Benzyloxy-3-t-butyldiphenylsilyloxypropan-2-ol

A solution of (S)-1-benzyloxy-3-t-butyldiphenylsilyloxypropan-2-ol (5 g, 11.9 mmol), triphenylphosphine (3.93 g, 15 mmol) and formic acid (0.7 g, 0.57 ml, 15.2 mmol) in dry tetrahydrofuran (50 ml) was cooled to 0° to 5° C. and treated with a solution of diethyl azodicarboxylate (2.61 g, 2.35 ml, 15 mmol) in dry tetrahydrofuran (15 ml). The solution was stirred overnight at room temperature and then treated with 35% aqueous ammonia to bring the pH to 11 (5 ml). The solution was stirred overnight and the solvent was evaporated in vacuo and purified by column chromatography on silica, eluting with 5% acetone in hexane (yield 4.7 g). A small amount (5%) of re-arranged material (resulting from silyl migration to the secondary hydroxyl group) was detected in the $^1$H NMR. The mixture was dissolved in dry tetrahydrofuran (3 ml) and imidazole (0.076 g, 1.1 mmol) was added. The mixture was then treated with t-butyldiphenylsilyl chloride (0.3 g, 1.1 mmol) and stirred at room temperature for 3 hours. The solvent was evaporated and the residue was purified by column chromatography on silica, eluting with hexane/ethyl acetate (90:10) to give the title compound as a colourless oil (4.2 g, 84%). $\upsilon_{max}$ (film) 3450, 3060, 2920, 2860, 1470, 1450, 1430, 1390, 1360 and 1110 cm$^{-1}$; $^1$H NMR: $\delta_H$[(CD$_3$)$_2$SO] 0.97 (9H, s, CH$_3$×3), 3.45 (1H, m, CH of CH$_2$), 3.58 (1H, m, CH of CH$_2$), 3.60 (2H, m, CH$_2$) 3.77 (1H, m, CH), 4.5 (1H, s, CH$_2$), 4.85 (1H, d, J=5Hz,D$_2$O exchangeable, OH), 7.25–7.5 (11H, m, ArH), 7.70 (4H, m, ArH). Found: C, 74.16; H, 7.57%; C$_{26}$H$_{32}$O$_3$Si requires: C, 74.24; H, 7.67 MS (70eV) m/z 421 (MH+); [α]D$^{25}$ = +1.9° (CHCl$_3$).

(b) (R) or (S)-1-Benzyloxy-3-t-butyldiphenylsilyloxypropan-2-trifluoromethanesulphonate A solution of (R) or (S)-1-benzyloxy-3-t-butyldiphenylsilyloxypropan-2-ol (4.2 g, 10 mmol) and 4-dimethylaminopyridine (1.35 g, 11mmol) in dry dichloromethane (50 ml) was treated with trifluoromethanesulphonic anhydride (3.1 g, 11 mmol) at 0°–5° C. The mixture was stirred for 1 hour and then washed with cold water (2 × 50 ml) and dried (MgSO$_4$). After filtration and evaporation in vacuo the residue was purified by column chromatography on silica gel, eluting with ethyl acetate/hexane (5:95) to give the title compound as a colourless oil (4.4 g, 80%). $\upsilon_{max}$ (film) 2956, 2935, 2860, 1253, 1181 and 1079 Cm$^{-1}$; $^1$H NMR $\delta_H$ (CDCl$_3$)

1.04 (9H, s, CH$_3$×3), 3.74 (2H, d, J TM 5Hz, CH$_2$O), 3.87 (2H, dd, J=5 and 2Hz, CH$_2$O), 4.53 (2H, s Ph CH$_2$O), 5.04 (1H, m, CH) 7.25-7.8 (15H, m, ArH); [α]D$^{25}$ CHCl$_3$) (S)-enantiomer=−4.8°, (R)-enantiomer=+5.4°.

(c) (R) or (S) Diethyl 1-Benzyloxy-3-t-butyldiphenylsilyloxypropan-2-thiomethylphosphonate A solution of diethylthiomethylphosphonate (1.33 g, 7.2 mmol) in dry tetrahydrofuran (50 ml) was treated with sodium hydride (0.175 g 7.2 mmol) at 0°-5° and stirred at room temperature for 1 hour. The solution was then cooled to 0°-5° and a solution of (R) or (S)-1-benzyloxy- 3-t-butyldiphenylsilyloxypropan-2-trifluoromethanesuphonate (4.0 g 7.2 mmol) in dry tetrahydrofuran (20 ml) was added dropwise over 10 min. The reaction mixture was then stirred for 18 hr at room temperature. The solvent was removed in vacuo and the residue was purified by column chromatography on silica, eluting with ethyl acetate/hexane (20:80) to give the title compound as a colourless oil (2.8 g, 66%); $\nu_{max}$ (Film) 3067, 2977, 2929, 2856, 1471, 1453, 1427, 1389, 1361, 1253 and 1112 cm$^{-1}$; $\delta_H$ (CDCl$_3$) 1.01 (9H, s, CH$_3$×3), 1.29 (6H, t, J TM 7Hz 2×CH$_3$CH$_2$), 2.75 (2H, dd, J=13.5 and 2Hz, PCH$_2$S), 3.24 (1H, m, CH), 3.78 (2H, m, CH$_2$), 3.9 (2H, m, CH$_2$), 4.11 (4H, m, 2×CH$_2$CH$_3$), 4.53 (2H, s, PhCH$_2$), 7.25-7.5 (11H, m, ArH) 7.68 (4H, m, ArH). (Found: C,63.45; H 7.44%; MS.(70eV): m/z TM 587 (MH+). C$_{31}$H$_{43}$O$_5$PSSi requires: C,63.45; H,7.38%) (MH+). CHCl$_3$) (R)-enantiomer=+1.03°; (S)-enantiomer=0°.

(d) (R) or (S)-Diethyl 3-t-butyldiphenylsilyloxy-3-hydroxypropan-2-thiomethylphosphonate To a solution of (R)- or (S)-diethyl benzyloxy-3-t-butyldiphenylsilyloxy-2-thiomethylphosphonate (1.1 g, 1.8 mmol) in 95% methanol/water (30 ml), was added 10% palladium on carbon (3 g) under a nitrogen atmosphere. The mixture was then hydrogenated at standard temperature and pressure until uptake of hydrogen ceased. The solution was filtered and the solvent was removed in vacuo. The residue was then purified by column chromatography on silica, eluting with hexane/ethylacetate (90:10) to give the title compounds as colourless oils. (0.56 g, 60%); $\nu_{max}$ (film) 3400, 2930, 2850, 1470, 1425, 1390, 1240 and 1110 cm$^{-1}$; $\delta_H$ (CDCl$_3$) 1.05(9H, s, CH$_3$×3), 1.32 (6H, t, J=7Hz, C$_3$CH$_2$×2) 2.75 (2H, m, PCH$_2$S), 3.1 (1H, m, CH), 3.75-4.0 (4H,m,CH$_2$×2) 4.1 (4H, in CH$_3$CH$_2$×2), 7.3-7.5 (6H, m, ArH), 7.65 (4H, m, ArH). (Found: C, 57.98; H, 6.97% C$_{24}$H$_{37}$O$_5$PSSi requires: C,58.03; H,7.51%; MS(70eV): m/z=497(MH+). [α]D$^{25}$ CHCl$_3$) (R)-enantiomer=+8.5°; (S)-enantiomer=−6.9°.

EXAMPLES

The compound of formula (I) prepared were as follows:

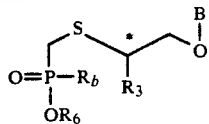

| Compound/Ex No. | B | R$_b$ | R$_3$ | R$_6$ |
|---|---|---|---|---|
| 1 | G | EtO | H | Et |
| 2 | G | HO | H | H |
| 3 | A | EtO | H | Et |
| 4 | A | HO | H | H |
| 5 | G | EtO | CH$_2$OH | Et |
| 6 | G | HO | CH$_2$OH | H |
| 7 | A | EtO | CH$_2$OAc | Et |
| 8 | A | EtO | CH$_2$OH | Et |
| 9 | A | HO | CH$_2$OH | H |
| 10 | A | —OCH$_2$— | | Na+ |
| 11 | G | —OCH$_2$— | | Na+ |
| 12 | G | HO | CH$_2$OH | H (R)-isomer |
| 13 | G | HO | CH$_2$OH | H (S)-isomer |

G = guanine
A = adenine

EXAMPLE 1

9-[2-(Diethoxyphosphorylmethylthio)ethoxy)quanine (a) A solution of 4-chloro-6-[(2-diethoxyphosphorylmethylthio)ethoxy]amino-2,5-diformamidopyrimidine (0.9 g, 2.0 mmol) in diethoxymethylacetate (2 ml) was heated to 120° C. for 2.5 hours. The cooled reaction was evaporated in vacuo. The residue was dissolved in methanol (5 ml), treated with ammonia solution (0.880,1 ml) and allowed to stand for 15 minutes at room temperature. The solvent was evaporated in vacuo and the residue was purified by column chromatography on silica gel eluting with dichloromethane: methanol (98:2) followed by crystallisation from diethyl ether/acetone to give 6-chloro-9-[(2-diethoxyphosphorylmethylthio)ethoxy]-2-formamidopurine (0.8 g, 93%) as colourless crystals, m.p. 74°-5° C.; λ$_{max}$ (MeOH) 232, 255 and 292nm (ε$s$ 10,454, 3556 and 4103), $\nu_{max}$ (KBr) 3200, 3100, 2960, 2900, 1685, 1600, 1570, 1500, 1475 and 1430 cm$^{-1}$; $\delta_H$[(CD$_3$)$_2$SO]1.23 (6H, t, J 6.5Hz 2 × CH$_3$), 3.0 (2H, d J 13Hz, PCH$_2$S), 3.1 (2H, t, J6.5Hz, CH$_2$S), 4.0 (4H, m, 2 × CH$_2$OP), 4.6 (2H, t, J 6.5Hz, CH$_2$ON) 8.7 (1H, s, 8-H), 9.4 (1H, br.s, CHO), 11.3 (1H br.s, D$_2$O exchangeable NH) (Found: C, 36.58; H, 4.51; N, 16.17%; M+ 423.0527, C$_{13}$H$_{19}$N$_5$O$_5$PSCl requires C, 36.84; H, 4.52; N, 16.52%; M+ 423.0533).

(b) A solution of 6-chloro-9-[2-(diethoxyphosphorylmethylthio)ethyl]2-formamidopurine (0.7 g, 1.65 mmol) in 80% formic acid (10ml) was heated to 80° C. for 1.5 hours. The cooled solution was evaporated in vacuo and the residue was dissolved in methanol, treated with 0.880 ammonia (1ml) and allowed to stand for 15 minutes at room temperature. The solvent was evaporated in vacuo and the residue was purified by chromatography on silica gel, eluting with dichloromethane: methanol (95:5), followed by crystallisation from methanol/water to give the title compound as colourless crystals (0.4 g, 64%), m.p. 190°-91° C.; λ$_{max}$ (EtOH) 255nm (ε14,391); $\nu_{max}$ (KBr) 3320, 3150, 2970, 2870, 2840, 2730, 1690, 1640, 1600, 1570, 1530 and 1470 cm$^{-1}$ $\delta_H$ [(CD$_3$)$_2$SO]1.23 (6H, t, J 7Hz, 2 × CH$_3$), 3.01 (2H, t, J 6.5Hz, SCH$_2$), 3.03 (2H, d, J 13Hz PCH$_2$S), 4.03 (4H, m, 2 × CH$_2$OP), 4.5 (2H, t, J 6.5Hz, CH$_2$ON,), 6.6 (2H, br.s, D$_2$O exchangeable NH$_2$). 7.9 (1H, s, 8-H), 10.6 (1H, br.s, D$_2$O exchangeable NH), (Found: C, 37.41, H, 5.22; N, 18.29%, m/z (thioglycerol) 378 (MH+ 100%). C$_{12}$H$_2$O N$_5$SP. 0.5H$_2$O requires C, 37.30; H, 5.40; N, 18.12%).

EXAMPLE 2

9-2-(Phosphonomethylthio)ethoxy)cuanine

Method 1

Trimethylsilylbromide (1.62 g, 10.6 mmol) was added to a solution of 9-[2-(diethoxyphosphorylmethylthio)ethoxy]-guanine (0.4 g, 1.06 mmol) at room temperature and the reaction mixture was allowed to stand for 3 hours. The solvent was evaporated in vacuo and the residue was dissolved in methanol, allowed to stand for 5 minutes. The methanol was evaporated in vacuo and the residue solidified and was crystallised from water to give the title compound as colourless crystals (0.08 g, 23%), m.p. 253°-3° C.; $\gamma_{max}$ (EtOH) 255nm ($\epsilon$ 11,857); $\upsilon_{max}$ (KBr) 3310, 3120, 2900, 2740, 1745, 1705, 1660, 1630, 1550, 1470, and 1410 cm$^{-1}$; 6H [(CD$_3$)2SO] 2.7 (2H, d, J 13Hz PCH$_2$S), 3.0 (2H, t, J 6.5Hz, CH$_2$S), 4.4 (2H, t, J 6.5Hz, CH$_2$ON), 6.6 (2H, br.s, D$_2$O exchangeable NH) (Found: C, 30.23; H, 3.96; N, 21.63%. C$_8$H$_{12}$N$_5$O$_5$SP requires C, 29.90; H, 3.76; N, 21.80%).

Method 2

(a) A solution of 2-di-t-butoxycarbonylamino-9-hydroxy-6-methoxypurine (0.5 g 1.3 mmol), diethyl-2-hydroxyethylthiomethylphosphonate (0.3 g, 1.3 mmol) and triphenylphosphine (0.37 g, 1.4 mmol) in dry tetrahydrofuran (20 ml) was cooled to 0°-5° C. and treated with diethyl azodicarboxylate (0.25 g, 1.4 mmol). The reaction mixture was stirred at room temperature for 18 hours. The solvent was removed in vacuo and the residue was purified by column chromatography on silica gel eluting with ethyl acetate to give 9-[(2-diethoxyphosphorylmethylthio)ethoxy]-2-di-t-butoxycarbonyl-6-methoxypurine as a gum (0.51 g, 65%); $\upsilon_{max}$ (Film) 2960. 2890. 2850, 1790. 1760, 1690, 1470, 1390 and 1365 cm$^{-1}$; $\delta_H$ [(CD$_3$)2SO] 1.22 (6H, t, J 7Hz 2 × CH$_3$), 1.4 (18H, s, 6 × CH$_3$), 3.0 (2H, d, J 13Hz PCH$_2$S), 3.06 (2H, t, J 7Hz CH$_2$CH$_2$S), 4.05 (4H, m, CH$_2$OP), 4.07 (3H, s, OCH$_3$), 4.6 (2H, t, J 7Hz OCH$_2$CH$_2$) 8.7 (1H, s 8-H) (Found: C, 46.20; H, 6.56; N, 11.34%. C$_{23}$H$_{38}$N$_5$O$_9$SP requires C, 46.69:; H, 6.47; N, 11.84%).

(b) A solution of 9-[2-(diethoxyphosphorylmethylthio)ethoxy]2-di-t-butoxycarbonylamino-6-methoxypurine (0.51 g, 0.84 mmol) in dry dichloromethane (10 ml) at room temperature was treated with trimethylsilylbromide (2.57 g), 16.8 mmol) and the mixture was stirred for 3 hours at room temperature. The solvent was removed in vacuo and the residue was dissolved in methanol, evaporated to dryness and the residue was crystallised from water to give the title compound (0.2 g, 77%) m.p. 253°-55° C.

EXAMPLE 3

9-[2-(Diethoxyphosphorylmethylthio)ethoxy)adenine (a) A mixture of 9-hydroxy-6-phthalimidopurine (0.5 g, 2.2 mmol). diethyl-2-hydroxyethylthiomethylphosphonate (0.45 g. 2 mmol) and triphenylphosphine (0.52 g, 2 mmol) was dissolved in dry tetrahydrofuran (20 ml) and cooled to 0°-5° C. A solution of diethylazodicarboxylate (0.348 g, 2.0 mmol) in dry tetrahydrofuran (10 ml) was added dropwise with stirring, and after the addition was completed the reaction was stirred at room temperature for 18 hours. The solvent was then removed in vacuo, and the residue was purified by column chromatography on silica using ethyl acetate: methanol (98:2) as eluent to give 9-[2-(diethoxyphosphorylmethylthio)ethoxy]-6-phthalimidopurine (0.45 g 56%) as a white solid after crystallisation from acetone/diethyl ether, m.p. 115°-116° C.; $\gamma_{max}$ (EtOH) 271mm (s 14020) $\upsilon_{max}$ (KBr) 3100, 3060, 2960, 2900, 1780, 1725, 1650, 1600, 1580, 1453, 1400, 1380, 1360, 1320, 1280, 1240, and 1200 cm$^{-1}$; $\delta_H$ [(CD$_3$)$_2$SO] 1.25 (6H, t, J 7Hz 2 × CH$_3$), 3.0 (2H, d, J 13Hz, PCH$_2$S), 3.1 (2H, t, J 7Hz CH$_2$O, 4.0 (4H, m, 2 × CH$_2$), 4.7 (2H, t, J 7Hz, CH$_2$S), 8.1 (4H, m, Ar H), 9.0 (1H, s, 2H), 9.1 (1H, s, 8-H). (Found C, 48.65; H, 4.55; N, 14.23%. C$_{20}$H$_{22}$N$_5$O$_6$PS requires C,48.87; H, 4.51; N, 14.25%).

(b) A solution of 9-[2-(diethoxyphosphorylmethylthio)ethoxy]-6-phthalimidopurine (0.56 g, 1.lmmol) was cooled to 0°-5° C. and treated with N-methylhydrazine (0.86 g, 1.8 mmol). The mixture was stirred for 1 hour, and then filtered and the solvent was removed in vacuo. The residue was purified by column chromatography on silica gel, using dichloromethane: methanol (97:3) as eluent, to give the title compound (0.3 g, 75%) as colourless crystals after b crystallisation from acetone, m.p. 93°-95° C.; $\gamma_{max}$ (MeOH) 260nm ($\epsilon$ 12670); $\upsilon_{max}$ (KBr) 3360, 3280, 3140, 2995, 1685, 1610, 1570, 1480, 1410, 1370, 1330, 1300, and 1260cm$^{-1}$; 6H [(CD$_3$)2SO]1.25 (6H. t, J 8Hz 2 × CH$_3$), 3.0 (2H, d, J 13Hz PCH$_2$S), 3.1 (2H, t, J 7Hz, CH$_2$O), 4.1 (4H, m, 2 × CH$_2$), 4.6 (2H, t, J 7Hz, CH$_2$S), 7.4 (2H, br.s, exchangeable with D$_2$O, NH$_2$), 8.15 (1H, s, 2-H), 8.4 (1H, s, 8-H) (Found: C, 39.84; H, 5.51; N, 19.26%; M+ , 361.0981. C$_{12}$H$_2$O N$_5$O$_4$PS requires C, 39.88; H, 5.58; N, 19.38%; M+ , 361.0974).

EXAMPLE4

9-[2-(Phosphonomethylthio)ethoxy)adenine

A solution of 9-[2-(diethoxyphosphorylmethylthio)ethoxy]adenine (0.1 g, 0.27 mmol) in dry dichloromethane at room temperature was treated with bromotrimethylsilane (0.46 g, 30 mmol) and allowed to stand for 3 hours. The solvent was evaporated under reduced pressure and the residue was dissolved in methanol and allowed to stand for 5 minutes. The solvent was removed in vacuo and the residue was crystallised from water to give the title compound (0.06 g, 71%) as colourless crystals, m.p. 211°-13° C.; $\upsilon_{max}$ (KBr) 3060, 2960, 1695, 1600, 1555, 1470, 1450, 1400, 1350 and 1300 cm$^{-1}$; 6H [(CD$_3$)2SO] 2.7 (2H, d J 13Hz. PCH$_2$S), 3.1 (2H, t J 6.5Hz, CH$_2$O), 4.6 (2H, t J 6.5Hz CH$_2$S), 7.4 (2H, br.s, exchangeable with D$_2$O, NH$_2$), 8.15 (1H, s, 2-H), 8.4 (1H, s, 8-H). (Found: C, 31.58; H, 3.92; N, 23.26%. C$_8$H$_{12}$N$_5$O$_4$PS requires C, 31.47; H, 3.96; N, 22.95%).

EXAMPLE 5

9-[3-Hydroxy-2-diethoxyphosphorylmethylthio)-propoxy]-guanine (a) A solution of 2-bis-t-butoxycarbonylamino-9-hydroxy-6-methoxy-purine (0.7 g, 1.8 mmol), diethyl-1-acetoxy-3-hydroxypropan-2-thiomethylphosphonate. (0.55 g, 1.8 mmol), and triphenylphosphine (0.75 g, 2.8 mmol) in dry tetrahydrofuran (20 ml) was cooled to 0°-5° C. and treated with diethyl azodicarboxylate (0.48 g, 2.75 mmol). The solution was stirred overnight then the solvent was removed in vacuo. The residue was purified by column chromatography on silica, using ethyl acetate as eluent, to give 9-[3-acetoxy-2-(diethoxyphosphoryl-methylthio)propoxy]-2-di-t-butoxycarbonylamino-6-methoxypurine as a yellow oil (1.0 g, 85%), $\lambda_{max}$ (EtOH) 256nm ($\epsilon$ 12410); $\upsilon_{max}$ (Film) 3110, 2990, 2940, 1795, 1750, 1720, 1600, 1475, 1460, 1425, 1395 and 1370 cm$^{-1}$; $\delta_H$ [(CD$_3$)$_2$SO] 1.21 (6H, t, J 7Hz 2 × CH$_3$) 1.4 (18H, s, 6 × CH$_3$) 2.03 (3H, s, COCH$_3$), 3.1 (2H, d, J 13Hz PCH$_2$S), 3.6 (1H, m, CH), 4.01 (4H, m, 2 × CH$_2$), 4.07 (3H, s, OCH$_3$), 4.4 (2H, m,CH$_2$OAc), 4.6 (2H, m, CH$_2$). (Found C, 47.25; H, 6.37; N, 10.40%. C$_{26}$H$_{42}$N$_5$O$_{11}$PS requires C,47.05, H, 6.38; N, 10.55%).

(b) A solution of 9-[3-acetoxy-2-(diethoxy-phosphorylmethylthio)propoxy]2-di-t-butoxycarbonylamino-6-methoxypurine (0.6 g, 0.9 mmol) in ethanol was treated with 0.5 ml 5N hydrochloric acid and then heated under reflux for 5 hours. The solution was cooled, neutralised with AMBERLITE IR 240H resin, filtered and the solvent removed in vacuo. The residue was purified by column chromatography on silica, using methanol:dichloromethane (20:80) as eluent, followed by crystallisation from methanol/acetone to give the title compound as colourless crystals (0.15 g, 41%, m.p. 144°-46° C.); $\lambda_{max}$ (EtOH) 254 ($\epsilon$ 19,200), 265nm ($\epsilon$ 16,150); $\upsilon_{max}$ (KBr) 3320, 3160, 2980, 2920, 2360, 2230, 1690, 1650, 1600, 1580, 1535, 1470, 1380, and 1330 cm$^{-1}$; $\delta_H$[(CD$_3$)$_2$SO]1.25 (6H, t, J 7.0Hz 2 × CH$_3$), 3.0 (2H, d, J 13.7Hz, PCH$_2$S), 3.75 (2H, m,CH$_2$OH), 4.1 (4H. m, 2 × CH$_2$), 4.4, (2H, m, OCH$_2$), 5.0 (1H, t, J=5.5Hz, CH$_2$CH), 6.6 (2H, br.s, exchangeable with D$_2$O, NH$_2$) 7.9 (1H, s, 8-H), 10.6 (1H, br.s, exchangeable with D$_2$O, NH), m/z (f.a.b. +ion NoBA) 408 (MH+) (Found: C, 37.93; H, 5.40; N, 17.22%. C$_{13}$H$_{22}$N$_5$O$_6$PS requires C, 38.24; H, 5.44; N, 17.19%).

EXAMPLE 6

9-3-Hydroxy-2-(phosphonomethylthio)propoxy1guanine

A solution of 9-[3-hydroxy-2-(diethoxyphosphorylmethylthio)propoxy]guanine (0.15 g, 0.36 mmol) in dry dimethylformamide (20 ml) at room temperature, was treated with bromotrimethylsilane (lml, 7.5 mmol) and the reaction was stirred for 3 hours. The solvent was removed in vacuo and the residue was dissolved in methanol (20 ml) and evaporated in vacuo to leave a clear gum. This was purified by column chromatography on C$_{18}$ silica using water as eluent, the relevant fractions were concentrated in vacuo and the product crystallised from water to give the title compound (0.05 g, 41%), m.p. 201°-203° C.; $\lambda_{max}$ (H$_2$O ) 253nm ($\epsilon$ 13,140); $\upsilon_{max}$ (KBr) 3300, 3130, 2900, 2320, 1710, 1640, 1590, 1450, and 1370 cm$^{-1}$; $\delta_H$[CD$_3$)$_2$SO] 2.75 (2H, dd, J 14 and 2Hz PCH$_2$S), 3.3 (1H, m, CH), 3.7 (2H, m, CH$_2$O), 4.4 (2H, m,CH$_2$OH), 6.6 (2H, br.s, exchangeable with D$_2$O, NH$_2$), 7.9 (1H, s, 8-H), 10.7 (1H, br.s, exchangeable with D$_2$O, NH) m/z (f.a.b. + v ion,; thioglycerol) 352 (MH+) (Found: C, 30.00; H, 4.19; N, 19.49%. C$_9$H$_{14}$N$_5$O$_6$PS. 0.5H20 requires C, 30.77; H, 4.01; N, 19.93%).

EXAMPLE 7

9-[3-Acetoxy-2-(diethoxyphosphorylmethylthio)-propoxy]-adenine (a) A mixture of 9-hydroxy-6-phthalimidopurine (0.53 g, 1.8 mmol), diethyl-1-acetoxy-3-hydroxypropan-2-thiomethylphosphonate (0.56 g, 1.8 mmol), and triphenylphosphine (0.56 g, 2.lmmol) in dry dimethylformamide (20 ml) was cooled to 0°-5° C. and treated with diethylazodicarboxylate (0.37 g, 2.lmmol). The reaction was stirred at room temperature for 18 hours, and then the solvent was removed in vacuo. The residue was purified by column chromatography on silica using ethyl acetate then 95:5 ethylacetate: methanol, to give 9-[3-acetoxy-2-(diethoxyphosphorylmethylthio)propoxy]-6-phthalimidopurine as a yellow oil (0.7 g, 70%), $\lambda_{max}$ (EtOH) 271nm ($\epsilon$ 14,815); $\upsilon_{max}$ (Film) 3580, 3450, 3100, 3050, 2970, 2920, 1790, 1730, 1595, 1575, 1450, 1400 and 1300 cm$^{-1}$; $\delta_H$ [(CD$_3$)$_2$SO] 1.22 (6 $_H$, t, J 7Hz, 2 × CH$_3$), 2.1 (3H, s, CH$_3$CO), 3.2 (2H, dd, J 14 and 2Hz, PCH$_2$S), 3.7 (1H, m, CH), 4.1 (4H, m, 2 × CH$_2$), 4.5 (2H, m, CH$_2$O) 4.75 (2H, m, CH$_2$OAc), 8.1 (4H, m, ArH) 9.0 (1H, s, 2-H), 9.1 (1H, s, 8-H). (Found: C, 49.21:; H, 4.93; N, 12.24%; M+ , 563.1267. C$_{23}$H$_{26}$N$_5$O$_8$PS requires C,49.02; H, 4.65; N, 12.43%; M;, 563.1240).

(b) A solution of 9-[3-acetoxy-2-(diethoxy-phosphorylmethylthio)propoxy]-6-phthalimidopurine (0.7 g, 1.24 mmol) in dichloromethane was cooled to 0°-5° C. and treated with N-methylhydrazine (0.085 g, 1.84 mmol). The solution was stirred for 2 hours, filtered, and the solvent was evaporated in vacuo. The residue was purified by column chromatography on silica to give 9-[3-acetoxy-2-(diethoxyphosphorylmethylthio)propoxy]-6-phthalimidopurine (0.4 g, 75%) as a colourless gum; $\lambda_{max}$ (EtOH) 260nm ($\epsilon$ 13,820); $\upsilon_{max}$ (Film) 3330, 3190, 2990, 2910, 1745, 1640, 1600, 1470, 1450, 1412, 1390, and 1330 cm$^{-1}$; $\delta_H$[CD$_3$)$_2$SO] 1.2 ($\delta_H$ , t, J 7Hz 2 × CH$_3$), 2.1 (3H, s, CH$_3$), 2.1 (3H, s, CH$_3$CO), 3.1 (2H, d, J 13.5Hz, PCH$_2$S), 3.6 (1H, m, CH), 4.0 (4H, m, 2 × CH$_2$), 4.4 (2H, m, CH$_2$O), 4.6 (2H, m,CH$_2$OAc), 7.4 (2H, br.s, exchangeable with D$_2$O, NH$_2$) 8.1 (1H, s, 2-H), 8.4 (1H, s, 8-H) (Found: C, 41.07; H, 5.72; N, 15.67%, M+ , 433.1196. C$_{15}$H$_{24}$N$_5$O$_6$PS requires C, 41.56; H, 5.58; N, 16.16%; M+ , 433.1185).

EXAMPLE 8

9-[3-Hydroxy-2-(diethoxyphosphorylmethylthio)-cropoxy1-adenine

A solution of 9-[3-acetoxy-2-(diethoxyphosphorylmethylthio)propoxy]adenine (0.4 g, 0.92 mmol) in ethanol (10 ml) was treated with 5M hydrochloric acid solution (0.4 ml, 2.0 mmol) and heated under reflux for 5 hours. The cooled solution was neutralised with AMBERLITE IR 45 OH resin and the solution was filtered and evaporated in vacuo. The residue was purified by column chromatography on silica, using chloroform : methanol (95:5) as eluent, to give the title compound (0.3 g, 83%) as a colourless gum; $\lambda_{max}$ (EtOH) 260nm ($\epsilon$ 13,700); $\upsilon_{max}$ (Film) 3320, 3180, 2970, 2800, 1640, 1590, 1460, 1405, 1380, 1320 and 1290cm$^{-1}$; $\delta_H$ [(CD$_3$)$_2$SO] 1.2 ($\delta_H$ , t, J 7Hz, 2×CH$_3$); 3.1 (2H, d, J 13.5Hz, PCH$_2$S), 3.7 (1H, m, CH ofCH$_2$OH), 3.9 (1H, m, CH ofCH$_2$OH), 4.0 (4H, m, 2 × CH$_2$), 4.6 (2H, m, CH$_2$O), 5.2 (1H, t, J 5.5Hz, exchangeable with D$_2$O, OH), 7.4 (2H, br.s, exchangeable with D$_2$O, NH$_2$), 8.2 (1H, s, 2H), 8.4 (1H, s, 8-H); (Found C, 38.70, H, 5.75, N. 18.00%; M+ 391.1082. C$_{13}$H$_{22}$N$_5$O$_5$PS requires C, 39.90, H, 5.66, N, 17.90%; M+ 391.1079).

EXAMPLE 9

9-[3-Hydroxy-2-(phosphonomethylthio)propoxy]adenine

A solution of 9-[3-hydroxy-2-(diethoxyphosphorylmethylthio)propoxy]adenine (0.265 g, 0.67 mmol) in dry dichloromethane (20 ml) was treated with bromotrimethylsilane (1.53 g, 10 mmol) at room temperature and allowed to stand for 6 hours. The solvent was removed under reduced pressure and the residue was dissolved in methanol, before being allowed to stand for 5 minutes. The solution was evaporated to dryness under reduced pressure, re-dissolved in methanol, neutralized with AMBERLITE IR 45 OH resin and filtered and evaporated in vacuo. The residue was crystallised from water to give the title compound (180mg, 80%) as colourless crystals, m.p. 195°-97° C. $\lambda_{max}$ (H$_2$O) 260nm ($\epsilon$ 14,000) $\nu_{max}$ (KBr) 3320, 3110, 2920, 1720, 1595, 1550, 1490, 1460, 1405, 1340 and 1300 cm$^{-1}$; $\delta_H$ [(CD$_3$)$_2$SO] 2.70 (2H,d, J 13.5Hz, PCH$_2$S), 3.3 (1H, m, CH), 3.7 (1H, m, CH ofCH$_2$OH), 3.8 (1H, m, CH of CH$_2$OH), 4.6 (2H, m, CH$_2$O), 7.6 (2H, br s, exchangeable with D$_2$O, NH$_2$), 8.2 (1H, s, 2-H), 8.46 (1H, s, 8-H).

EXAMPLE 10

9-(2-Hydroxy-2-oxo-1,4,2-oxathiaphoschorinan-5-yl)-methoxyladenine, sodium salt

A solution of 9-[3-hydroxy-2-(phosphonomethylthio)propoxy]adenine (0.2 g, 0.59 mmol) and N,N-dicyclohexyl-4-morpholinocarboxamidine (0.175 g, 0.59 mmol) in 50:50 t-butanol: water (30 ml) was heated to gentle reflux. A solution of N,N-dicyclohexylcarbodiimide (0.615 g, 2.98 mmol) in t-butanol (13 ml) and dimethylformamide (2 ml) was then added, dropwise over 0.5 hour. The reaction mixture was then heated and stirred for a further 5.5 hours. The cooled reaction mixture was then evaporated in vacuo and the residue was dissolved in water and filtered. The filtrate was evaporated in vacuo and the residue was purified by column chromatography on Sephadex (DEAE, HCO$_3$ form), eluting with a linear gradient of triethylammonium carbonate buffer (0.001-0.2M); 15 ml fractions were collected and fractions 36-42 were bulked and evaporated in vacuo. The residue was co-evaporated with ethanol (20 ml) until no triethylamine could be detected (3×), the residue was dissolved in water and treated with Dowex 50 XA resin (Na+ form) to give the sodium salt. After filtration the solvent was concentrated in vacuo and lyophilised to give the title compound as a colourless powder (0.140 g, 69%), m.p. >300° C.; $\lambda_{max}$ (H$_2$O) 260.4 nm (14,350); $\nu_{max}$ (KBr) 3200, 2950, 2895, 1700, 1610, 1470, 1415, 1340, 1305 and 1190 cm$^{-1}$; $\delta_H$ [(CD$_3$)$_2$SO]2.60 (1H, t, J=15.4Hz, H of PCH$_2$S), 3.02 (1H, dd, J=11.2 and 10.2Hz, H of PCH$_2$S), 4.5-4.75 (4H, m, OCH$_2$ and OCH$_2$CH), 7.46 (2H, s, D$_2$O exchangeable NH$_2$), 8.16 (1H, s, 2-H), 8.44 (1H, s, 8-H), m/z (FAB +ve ion, thioglycerol), 340 (MH+) (Found: C, 32.22; H,3.49; N, 20.31% C$_9$H$_{11}$N$_5$O$_4$PSNa requires: C, 31.86; H, 3.26; N, 20.64%).

EXAMPLE 11

9-[(2-Hydroxy-2-oxo-1,4,2-oxathiaohosphorinan-5-yl)-methoxylquanine sodium salt

A solution of 9-[3-hydroxy-2-(phosphonomethylthio)-propoxy]guanine (0.2 g, 0.56 mmol) and N,N-dicyclohexyl-4-morpholinocarboxamidine (0.165 g, 0.56 mmol) in 50:50 t-butanol: water, was heated to gentle reflux. A solution of N,N-dicyclohexylcarbodiimide (0.58 g, 2.8 mmol) in t-butanol (13 ml) and dimethylformamide (2 ml) was then added dropwise over 0.5 hour. The mixture was then stirred and heated for a further 5.5 hours. The cooled reaction was evaporated in vacuo and the residue was dissolved in water and filtered The filtrate was evaporated in vacuo and the residue was purifed by column chromatography on DEAE Sephadex (HCO$^-$$_3$), eluting with a linear gradient of triethylammonium carbonate buffer (0.001-0.25M); 15 ml fractions were taken and fractions 35-48 were bulked and evaporated to dryness in vacuo. The residue was co-evaporated with ethanol (20 ml) until triethylamine was not detectable (3×) and then dissolved in water (25 ml) and treated with Dowex 50XA resin (Na+ form) to give the sodium salt. After filtration the solvent was concentrated in vacuo,affording the title compound as colourless crystals (0.150 g, 74%), m.p. >300° C.; $\lambda_{max}$ (H$_2$O ) 253.5 and 266 nm (9570 and 7610); $\nu_{max}$ (KBr) 3390, 1700, 1610, 1460, 1370, 1210, and 1170 cm$^{-1}$; $\delta_H$ [(CD$_3$)$_2$SO) 2.16 (1H, t, J=14Hz,H of PCH$_2$S), 2.6 (1H, dd, J=14 and 14Hz, H of PCH$_2$S), 2,85 (1H, m, CHS), 4.35-4.7 (4H, m, OCH$_2$ and OCH$_2$CH), 7.95 (1H, s, 8-H); m/z (FAB +ve ion thioglycerol), 356 (MH+) (Found: C, 28.48; H, 3.67; N, 18.44%. C$_9$H$_{11}$N$_5$O$_5$ PSNa. 1.5H$_2$O requires: C, 28.27; H, 3.66; N, 18.32%).

EXAMPLES 12 AND 13

(R) or (S)-9-[3-Hydroxy-2-(phosphonomethylthio)-propoxyl-quanine (a) A solution of 2-t-butoxyoarbonylamino-9-hydroxy-6-methoxypurine (0.39 g, 1.02 mmol) (R)- or (S)-diethyl-3-t-butyldiphenylsilyloxy-1-hydroxypropane-2-thio-methylphosphonate (0.5 g, 1.0 mmol) and triphenylphosphine (0.32 g, 1.22 mmol) in dry tetrahydrofuran (20 ml) was cooled to 0°-5° C., and a solution of diethyl azodicarboxylate (0.21 g 1.2 mmol) in dry tetrahydrofuran (5 ml) was added. The mixture was stirred at room temperature for 18 hr, then the solvent was evaporated in vacuo and the residue was purified by column chromatography on silica, eluting with ethyl acetate/hexane (30:70) to give (R) or (S) 9-[3-t-butyl-diphenylsilyloxy-2-(diethoxyphosphorylmethylthio)-propoxy]di-t-butoxycarbonylamino-6-methoxypurine as a pale yellow oil (0.5 g, 58%). $\nu_{max}$ (Film). 3070, 2980, 2930, 2860, 1795, 1760, 1590, 1470, 1425, 1390, 1365, and 1250 cm$^{-1}$; $^1$H NMR $\delta_H$ (CDCl$_3$) 1.06 (9H, s, CH$_3$×3), 1.3 ($\delta_H$ , t, J TM 7Hz, CH$_3$CH$_2$×2), 1.43 (18H, s, CH$_3$×6), 2.75 (2H, m, PCH$_2$S), 3.5 (1H, m, CH), 3.9-4.2 (9H, m, CH$_3$CH$_2$ ×2 +OCH$_3$ +CH$_2$) 4.7 (2H, m, CH$_2$), 7.3-7.5 (6H, m, ArH), 7.6-7.7 (4H, m, ArH). 8.0 (1H, s, 8-H). (Found: C,55.36; H, 6.86; N, 8.11%. C$_{40}$H$_{58}$N$_5$O$_{10}$PSSi requires: C, 55.96%; H,6.79; N,8.14%). [$\alpha$]D$^{25}$ (R)-enantiomer=+1.8°; (S)-enantiomer=-1.2°; MS. (70ev): m/z=860 (MH+).

(b) (R)- or (S)-9-[3-t-butyldiphenylsilyloxy-2-(diethoxyphosphorylmethylthio)propoxy]di-t-butoxycarbonylamino-6-methoxypurine (0.45%, 0.52 mmol) was added to a mixture of water (1.5 ml) and trifluoroacetic acid (4.5 ml), and the mixture was stirred at room temperature for 3 hr. The solution was then treated with saturated ethanolic ammonia solution to bring the pH to 11. The solution was extracted with chloroform (3×50 ml) and the organic layers were combined and dried (MgSO$_4$). After filtration and evaporation in vacuo the residue was purified by column chromatography on silica, eluting with chloroform : methanol (95:5) to give (R) or (S)-2-Amino-9-[2-(diethoxyphosphorylmethyl-thio)-3-hydroxypropoxy]-6-methoxypurine as a colourless gum (0.16 g, 72%). $\nu_{max}$ (film) 3340, 3220, 3120, 2980, 1620, 1585, 1500, 1480, 1450, 1390, 1330 and 1260 cm$^{-1}$; 1H NMR $\delta_H$ [(CD)$_3$SO] 1.22 ($\delta_H$ , t, J 6Hz, CH$_3$×2) 3.06 (2H,d, J=12.5Hz, PCH$_2$S), 3.35 (1H, m, CH of CH$_2$), 3.66 (1H, m, CH of CH$_2$), 3.8 (1H, m, CH),3.96 (3H, s, OCH$_3$), 4.02 (4H, m, CH$_2$×2), 4.46 (2H, m, CH$_2$), 5.06 (1H, t, J TM 5.5Hz, D$_2$O exchangeable OH), 6.6 (2H, brs, D$_2$O exchangeable NH$_2$), 8.1 (1H, s, 8-H): (Found: C, 39.03; H,5.70; N$_{15.89}$%. C$_{14}$H$_{24}$N$_5$O$_6$PS (0.5 H$_2$O ) requires: C,39.06; H,5.80, N,16.24%; MS.(70eV): m/z=422 (MH+); [α] 25 CHCl$_3$) (S)-enantiomer TM +1.8°; (R)-enantiomer= −1.3°.

(c) A solution of (R)- or (S)-2-amino-9-[2-(diethoxyphosphorylmethylthio)-3-hydroxypropoxy]-6-methoxy-purine (0.14 g, 0.33 mmol) in dry dichloromethane (20 ml) was treated with bromotrimethylsilane (0.86 ml, 1.0 g, 6.5 mmol) and the solution was allowed to stand at room temperature for 4 hr. The solvent was evaporated in vacuo and the residue was then purified using Sephadex chromatography, eluting with a linear gradient of triethylammonium carbonate buffer (0.001–0.6M) followed by crystallisation from methanol:water (95.5),to give the title compounds as colourless crystals (0.105 g, 90%). mp. >300° C.; $\lambda_{max}$ (H$_2$O) 254nm (12,563); $\nu_{max}$ (KBr) 3320, 3140, 1720, 1640, 1600, 1460,1390, and 1370 cm$^{-1}$; 1H NMR $\delta_H$ (CD$_3$)$_2$SO] 2.75 (2H, dd, J TM 13.5 and 2Hz, PCH$_2$S), 3.3 (1H, m, CH), 3.6 (1H, m, CH of CH$_2$), 3.8 (1H, m, CH of CH$_2$), 4.4 (2H, m, CH$_2$O) 6.6 (2H, br.s, D$_2$O exchangeable NH$_2$), 7.9 (1H, s, 8-H), 10.6 (1H, br.s, D$_2$O exchangeable NH); (Found: C,35.82; H,5.55; N,19.57%. C$_9$H$_{14}$N$_5$O$_6$PS (0.5 Et3N) requires: C,35.86; H,5.37; N,19.17%); MS.(70 eV) m/z TM 352 (MH+); [α]D$^{25}$ (H$_2$O) (S)-enantiomer=0°; (R)-enantiomer =0°.

ANTIVIRAL ACTIVITY

1. CPE Inhibition Test (Replicatinq Cells) for Herpes Simplex Virus 1

MRC-5 cells (in Eagle's MEM containing 5% newborn calf serum) were infected in suspension with herpes simplex virus 1, strain SC16 (approximately one infectious particle per 10 cells). One hundred microliters of the infected cell suspension (containing approximately 2×10$^4$ cells) were dispensed into each well of a 96 well microtitre plate containing an equal volume of the test compound in medium (Eagle's MEM containing 5% newborn calf serum) at concentrations ranging from 200 to 0.06 μg/ml prepared in 3-fold dilution steps; final concentrations therefore ranged between 100 and 0.03 μg/ml. The plates were then incubated at 37° C. in a humidified atmosphere containing 5% CO$_2$ for 3 days when the virus-induced cytopathic effect (CPE) in the control wells reached 100%. The plates were fixed in formol saline and stained with carbol fuchsin. The plates were then examined to find the concentration of test compound which reduced the virus-induced CPE by 50% (IC$_{50}$) Plates of uninfected cells were set up in parallel to determine the minimum concentration of test compound which caused cytotoxicity.

2. Placue Reduction Test for Herpes Simolex Virus 2

MRC-5 cells were grown to confluence in 24 well multi-dishes (well diameter=1.5cm). The drained cell monolayers were each infected with approximately 50 infectious particles of herpes simplex virus 2 (HSV-2; strain MS) in 100 μl of phosphate-buffered saline. The virus was adsorbed for 1 hour at room temperature. After adsorption, residual inoculum was removed from each well and replaced with 0.5 ml of Eagle's MEM containing 5% newborn calf serum and 0.9% agarose (A37). Once the agarose had set, dilutions of the test compound, which had been prepared in Eagle's MEM (containing 5% newborn calf serum), were added, each well receiving 0.5 ml of liquid overlay. The test compound was diluted to give the following series of concentrations: 200, 60, 20, 6 ... 0.06 μg/ml; final concentrations in the assay ranged, therefore, between 100 μg/ml and 0.03 μg/ml. The infected cultures wereincubated at 37° C. in a humidified atmosphere of 5% CO$_2$ until plaques were clearly visible (usually 1 day).

3 Plaoue Reduction Test for Varicella Zoster Virus

MRC-5 cells were grown to confluence in 24 well multi-dishes (well diameter=1.5cm). The drained cell monolayers were each infected with approximately 50 infectious particles of varicella zoster virus (VZV; Ellen strain) in 100 μl of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6 ... 0.06 μg/ml; final concentrations in the assay ranged, therefore, between 100 μg/ml and 0.03 μg/ml. The infected cultures were incubated at 37° C. in a humidified atmosphere of 5% CO$_2$ until plaques were clearly visible (5 or 6 days).

Cultures from tests 2 and 3 were fixed in formal saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occured Was recorded.

4 Plaque Reduction Test for Cytomegalovirus

MRC-5 cells were grown to confluence in 24 well multi-dishes (well diameter=1.5cm). The drained cell monolayers were each infected with approximately 50 infectious particles of cytomegalovirus (CMV; AD-169 strain) in 100 μl of phosphate-buffered saline. The virus was adsorbed for 1 hour at room temperature. After adsorption, residual inoculum was removed from each well and replaced with 1ml of Eagle's MEM containing 10% heatinactivated foetal calf serum and 0.9% agarose (A37). Once the agarose had set, dilutions of the test compound, which had been prepared in Eagle's MEM (containing 10% heat-inactivated calf serum), were added, each well receiving 1ml of liquid overlay. The test compound was diluted to give the following series of concentrations: 200, 60, 20, 6 ... 0.06 μg/ml; final concentrations in the assay range, therefore, between 100 μg/ml and 0.03 μg/ml. The infected cultures were incubated at 37° C. in a humidified atmosphere containing 5% CO$_2$ until plaques were clearly visible (about 12 days). The cultures are fixed in formol saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occured was recorded.

5. CPE Inhibition Test (Established Monolayer) for Lentiviruses $3 \times 10^4$ sheep choroid plexus (SCP) cells were plated into individual wells of a 96 well microtitre plate in 100 µl of Eagle's MEM with Hanks' salts containing 10% heat inactivated foetal calf serum (FCS). When monolayers had become established (after 1 or 2 days growth) they were washed with 200 µl of maintenance medium (Eagle's MEM with Hanks' salts containing 0.5% FCS) and infected with 100 µl of visna virus (strain K184) in maintenance medium (30 TCID50/ ml). Test samples were diluted with maintenance medium in further 96 well microtitre plates over the range 200–0.06 µg/ml by 3-fold dilution steps. 100 µl of the diluted samples was then transferred directly onto virus-infected monolayers (final concentration range therefore 100–0.03 µg/ml) and incubated at in a humidified atmosphere containing 5% $CO_2$ until virus-induced CPE was maximal in the untreated virus-infected controls (usually 12–14 days). The plates were fixed with formal saline and stained with crystal violet. Virus-induced CPE was then scored microscopically and the minimum concentration of sample giving complete protection of the cell monolayers (MIC) determined.

6. Test for Human Immunodeficiencv Virus (HIV)

(a) Cell cytotoxicity test

Peripheral human lymphocytes were isolated by density gradient centrifugation from blood donations of healthy volunteers. The 'buffy coat' fractions of these donations were provided by blood donation centres.

The buffy coat was diluted 1:1 with sterile phosphate buffered saline (PBS: 50 mM sodium phosphate. pH 7.4, 0,9% sodium chloride) and subsequently layered over Ficoll. Following centrifugation (30 minutes at 400 × g) the supernatant was discarded and the interphase containing the lymphocytes was recovered. The lymphocytes were washed two times in PBS and were resuspended finally in cell culture medium.

A viability staining was performed by means of the trypan blue dye-exclusion method. The concentration of cells in the suspension and the percentage of viable cells were calculated. Subsequently, the cell suspension was adjusted to a concentration of $1 \times 10^7$ cells/ml. This cell suspension was transferred to tissue culture flasks: Two thirds of the cell suspension were polyclonally activated by addition of phytohemagglutinin (final concentration 5 µg.ml). One third of the cell suspension remained unstimulated.

The lymphocytes were cultivated in an incubator with a humidified atmosphere and 5% $CO_2$ for 48 to 64 hours at 37° C. Following this incubation period, cells were harvested by centrifugation, resuspended in cell culture medium and counted. Stimulated and unstimulated cells were combined in a ratio of 2:1 and adjusted to a concentration of $2 \times 10^6$ cells/ml with cell culture medium that contained, in addition, 10 units/ml of human recombinant interleukin-2.

Only those preparations of lymphocytes were employed for the screening test in which more than 70% of the stimulated lymphocytes expressed the CD 25 antigen and more than 45% of the lymphocytes expressed the CD 4 antigen.

100 µg of this lymphocyte suspension was added to each well of microtiter plates containing the test compounds serially diluted over the range 100 µM to 0.1µM. Subsequently, the microtiter plates were cultivated for 4 days at 37° C.

Survival and proliferation of the lymphocytes grown in the presence of the compound were measured by a quantitative colorimetric assay. Viable cells cultivated in the presence of the dye MTT [3-4,5-dimethylthiazol-2-yl)-3,5-diphenyltetrazolium) reduce this pale yellow substrate by activity of their mitochondrial dehydrogenases to a purple formazan. The amount of product which is a function of cell number and metabolic cellular activity was quantified photometrically. By this assay, potential cytotoxic and cytostatic effects of compounds towards lymphocytes were detected precisely.

Microtiter plates were centrifuged for 5 minutes at 900 × g. The supernatant was discarded and the cells of each well were resuspended in 50 µl of cell culture medium containing 2 mg/ml of MTT. After four hours of incubation at 37° C. 100 µl of solvent (isopropanol with 0,04 N HCl and 10% (v/v) Triton 100) was added to each well. By shaking the microtiter plates the formazan was solubilized. Subsequently, the plates were evaluated in an ELISA photometer in the dual wavelength mode (measuring wavelength: 550 nm; reference wavelength: 690 nm).

For each well the difference in absorption (abs. 550 nm —abs. 690 nm) was calculated. These data provided the basis for further evaluation of the cytotoxicity test. The approximate $CD_{50}$ (halfmaximal cytotoxic dose) of each compound was calculated.

(b) HIV Suspression test

Peripheral human lymphocytes were prepared, cultivated, and harvested as above. Following the determination of the lymphocyte surface markers, unstimulated and mitogen stimulated cells were combined in a ratio of 1:2.

Under safety conditions these cells are infected with a standard preparation of HIV. The cells are sedimented by centrifugation. The supernatant was discarded and cells were resuspended in the HIV inoculum.

This inoculum is a liquid suspension of HIV-1 strain virus, pretested and adjusted to a titer that results in a synthesis of viral core protein p24 of > 100 ng/ml at day four following infection of human lymphocytes according to the protocol.

$3 \times 10^8$ lymphocytes were resuspended in 1 ml HIV inoculum and incubated at 37° C. for 60 minutes. Subsequently, the cells were washed two times with 50 ml of culture medium and resuspended in culture medium containing 10 units/ml of human recombinant interleukin-2 to yield a cell concentration of $2 \times 10^6$ cells/ml. 100 µl of this cell suspension was added to each well of the microtiter plates containing the diluted solutions of the compounds. The microtiter plates were cultivated in an incubator with a humidified atmosphere and 5% $CO_2$ at 37° C.

Accordingly, a fraction of lymphocytes was mock-infected with the same virus preparation that was heat inactivated (30 minutes at 56° C.) prior to infection.

On each of the days 2,3 and 4 post infection one of the microtiter plates which had been established in triplicate was prepared for determination of viral replication. Viral RNA is determined within the cells whereas the viral core protein p24 was detected in the supernatant of the lymphocyte culture.

Accordingly, 150 μl of supernatant were removed from each well and transferred to the well of a microtiter plate containing 50 μl well of SDS (sodium dodecylsulfate, 0.08%). These plates were stored frozen. 50 μl of stop solution (1% SDS, 20mM sodium acetate, pH 5.0, and 200 μg/ml heparin) were added to the cells remaining in each well. The plates were stored frozen.

The concentration of p24 synthesized by the HIV infected cells was determined by means of a sandwich ELISA, while the concentration of viral RNA was quantitated by nucleic acid hybridisation, using a 32P-labelled DNA probe for the gag/pol region of the viral genome. Absolute levels of viral antigen and RNA in drug treated samples were compared with untreated, virus-infected controls and the percentage inhibition calculated.

The results of the tests 1 to 5 were as follows:

| Antiviral Activity against DNA Viruses $IC_{50}$ (μg/ml) | | | |
|---|---|---|---|
| | Herpes Simplex Virus | Varicella Zoster | Cytomegalo- virus |
| Ex. No. | Type 1 SC16 Strain in MRC-5 Cells | Type 2 MS Strain in MRC-5 Cells | Virus Ellen Strain in MRC-5 Cells | AD169 Strain in MRC-5 Cells |
| 2 | 20 | 3.2 | 0.6 | 1.5 |
| 6 | 20 | >100 | 3.8 | 3.5 |
| 11 | >100 | >100 | 40 | 55 |
| 12 | 20 | NT | 4.1 | 4.3 |

At concentrations below 30 μg/ml, none of the compounds were cytotoxic for the cell monolayers used in the tests.

| Antiviral Activity against Visna Virus | |
|---|---|
| Ex. No. | MIC (μg/ml) |
| 2 | 1 |
| 4 | 30 |
| 6 | 0.1 |
| 9 | 100 |
| 10 | 100 |
| 11 | 0.3 |

| Antiviral Activity against HIV | | | | |
|---|---|---|---|---|
| | | % Inhibition on Days 3 and 4 after infection | | | |
| | | Viral Antigen | | Viral RNA | |
| Ex. No. | Concn. (μM) | Day 3 | Day 4 | Day 3 | Day 4 |
| 2 | 10 | 0 | 77 | 0 | 69 |
| 6 | 10 | 86 | 48 | 85 | 61 |

At the concentration tested (10 μM) neither compound was cytotoxic for uninfected peripheral human lympotcytes.

We claim:

1. A compound of formula (I), or a pharmaceutically acceptable salt thereof:

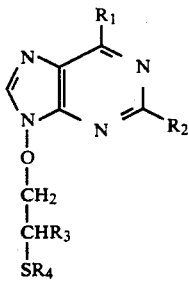

wherein
$R_1$ is hydroxy or amino;
$R_2$ is hydrogen or amio;
$R_3$ is hydrogen, hydroxymethyl or acyloxymethyl;
$R_4$ is a group of formula:

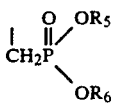

wherein
$R_5$ and $R_6$ are independently selected from hydrogen, $C_{1-6}$ alkyl and optionally substituted phenyl; or $R_3$ and $R_4$ together are

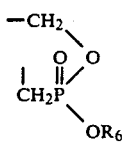

wherein
$R_6$ is as defined above.

2. A compound according to claim 1 wherein $R_1$ is hydroxy and $R_2$ is amino.
3. A compound according to claim 1 wherein $R_1$ is amino and $R_2$ is hydroqen.
4. A compound according to claim 1 wherein $R_3$ is hydroxymethyl.
5. A compound according to claim 1 wherein $R_5$ and $R_6$ are both hydrogen.
6. A compound selected from the group consisting of:
9-[2-(diethoxyphosphorylmethylthio)ethoxy)guanine,
9-[2-(phosphonomethylthio)ethoxy)guanine,
9-[2-(phosphonomethylthio)ethoxy)adenine,
9-[3-hydroxy-2-diethoxyphosphorylmethylthio)-propoxy]-guanine,
9-[3-hydroxy-2-(phosphonomethylthio)propoxy]guanine,
9-[3-acetoxy-2-(diethoxyphosphorylmethylthio)-propoxy]-adenine,
9-[3-hydroxy-2-(diethoxyphosphorylmethylthio)-propoxy]-adenine,
9-[3-hydrOxy-2-(phosphonomethylthio)propoxy]adenine,
9-[(2-hydroxy-2-oxo-1,4,2-oxathiaphosphorinan-5-yl)methoxy]adenine, sodium salt,
9-[(2-hydroxy-2-oxo-1,4,2-oxathiaphosphorinan-5-yl)methoxy]guanine sodium salt,
(R)-9-[3-hydroxy-2-(phosphonomethylthio)propoxy]-guanine and
(S)-9-[3-hydroxy-2-(phosphonomethylthio)propoxy]-guanine.
7. A pharmaceutical composition for use in treating viral infections caused by herpesviruses and lentiviruses and neoplastic diseases caused by tumorogenic viruses, comprising an effective amount of a compound according to claim 1, and a pharmaceutically acceptable carrier.
8. A method of treatment of viral infections caused by herpesviruses and lentiviruses and neoplastic diseases in mammals causes by tumorogenic viruses, which comprises the administration to mammals in need of such treatment, an effective amount of a compound according to claim 1.

* * * * *

UNITED STATES PATENT AND TRADEMARK OFFICE
CERTIFICATE OF CORRECTION

PATENT NO. : 5,108,994

DATED : April 28, 1992

INVENTOR(S) : Michael R. Harnden and Leslie J. A. Jennings

It is certified that error appears in the above-identified patent and that said Letters Patent is hereby corrected as shown below:

In Column 24, between lines 43 and 44, insert in claim 6 the compound

— 9-[2-(diethoxyphosphorylmethylthio)ethoxy]adenine —.

Signed and Sealed this

Twenty-second Day of June, 1993

Attest:

MICHAEL K. KIRK

Attesting Officer

Acting Commissioner of Patents and Trademarks